United States Patent
Ahmed et al.

(10) Patent No.: US 11,998,013 B1
(45) Date of Patent: Jun. 4, 2024

(54) 1-(MORPHOLIN-4-YL)-3-(NAPHTHALEN-2-YLOXY)PROPAN-2-OL AS AN ECO-FRIENDLY INSECTICIDAL AGENT AGAINST SPODOPTERA LITTORALIS (BOISD.)

(71) Applicant: KING FAISAL UNIVERSITY, Al-Ahsa (SA)

(72) Inventors: Hany Mohamed Abd El-Lateef Ahmed, Al-Ahsa (SA); Mai Mostafa Khalaf Ali, Al-Ahsa (SA); Antar Ahmed Abdelhamid Ahmed, Al-Baha (SA); Mohamed A. Gad, Giza (EG)

(73) Assignee: KING FAISAL UNIVERSITY, Al-Ahsa (SA)

( * ) Notice: Subject to any disclaimer, the term of this patent is extended or adjusted under 35 U.S.C. 154(b) by 11 days.

(21) Appl. No.: 18/241,382

(22) Filed: Sep. 1, 2023

(51) Int. Cl.
*A01N 43/84* (2006.01)
*A01N 25/12* (2006.01)
*A01P 7/04* (2006.01)
*C07D 295/088* (2006.01)

(52) U.S. Cl.
CPC .............. *A01N 43/84* (2013.01); *A01N 25/12* (2013.01); *A01P 7/04* (2021.08); *C07D 295/088* (2013.01)

(58) Field of Classification Search
CPC .......... A01N 43/84; A01N 25/12; A01P 7/04; C07D 295/088
USPC ....................................................... 514/239.2
See application file for complete search history.

(56) References Cited

U.S. PATENT DOCUMENTS 4,048,335 A    9/1977   Lucchesi

FOREIGN PATENT DOCUMENTS

WO    9313049 A1    7/1993
WO    2015004485 A1    1/2015

OTHER PUBLICATIONS

Fleischer et al., "Three-dimensional quantitative structure-activity relationship analysis of propafenone-type multidrug resistance modulators: influence of variable selection on test set predictivity", J Med Chem., Nov. 6, 2003; 46(23):4988-5004.

*Primary Examiner* — Kristin A Vajda
(74) *Attorney, Agent, or Firm* — Nath, Goldberg & Meyer; Richard C. Litman

(57) ABSTRACT

A compound 1-(morpholin-4-yl)-3-(naphthalen-2-yloxy)propan-2-ol, its synthesis, insecticidal compositions containing the same, and its use as an insecticidal agent.

18 Claims, 3 Drawing Sheets

1-(MORPHOLIN-4-YL)-3-(NAPHTHALEN-2-YLOXY)PROPAN-2-OL AS AN ECO-FRIENDLY INSECTICIDAL AGENT AGAINST SPODOPTERA LITTORALIS (BOISD.)

BACKGROUND

1. Field

The present disclosure relates to the compound 1-(morpholin-4-yl)-3-(naphthalen-2-yloxy)propan-2-ol, its synthesis, and its use as an insecticidal agent.

2. Description of the Related Art

According to the majority of difficulties caused by the use of pesticides and to lessen the impact of pesticide compounds, secure and unique selective organic components are required for development. Due to their clear mechanism of action on pests and lower poisonousness towards vertebrates than conventional insecticides, juvenile hormone analogs as an example of insect growth regulators appear promising. However, such new insect growth regulators are in their early stages of development and require further research and development.

Thus, new insecticides and/or pesticides solving the aforementioned problems are desired.

SUMMARY

The present subject matter relates to the synthesis of a unique pure insect growth regulator, as well as the regulator itself. The structure of this synthesized compound, which is related to the most well-known insect growth regulator insecticides, can be confirmed by elemental and contemporary spectroscopic investigations (IR, UV, $^1$HNMR, $^{13}$CNMR, and elemental analysis). The insecticidal efficacy of the chemically newly synthesized compound was checked against *Spodoptera littoralis* under laboratory conditions and compared with fenoxycarb as a reference insecticide. It has been found that the present compound has a $LC_{50}$=17.56 mg/l, whereas fenoxycarb has a $LC_{50}$=2.73 mg/l, indicating the insecticidal effectiveness of the present compound.

In an embodiment, the present subject matter relates to a 1-(morpholin-4-yl)-3-(naphthalen-2-yloxy)propan-2-ol compound having the formula I:

I

In another embodiment, the present subject matter relates to an insecticidally acceptable composition comprising an insecticidally effective amount of the 1-(morpholin-4-yl)-3-(naphthalen-2-yloxy)propan-2-ol compound and an insecticidally acceptable carrier.

In a further embodiment, the present subject matter relates to a method of killing insects comprising applying to said insects or to a target site of insect infestation an insecticidally effective amount of the 1-(morpholin-4-yl)-3-(naphthalen-2-yloxy)propan-2-ol compound or a composition containing the same.

In an additional embodiment, the present subject matter relates to a method of repelling insects comprising applying to a target site of insect infestation an insect repelling effective amount of the 1-(morpholin-4-yl)-3-(naphthalen-2-yloxy)propan-2-ol compound or a composition containing the same.

In one more embodiment, the present subject matter relates to a method of controlling an insect pest comprising applying to a target site of insect infestation an insect controlling effective amount of the 1-(morpholin-4-yl)-3-(naphthalen-2-yloxy)propan-2-ol compound or a composition containing the same.

In a further embodiment, the present subject matter relates to a method of making the 1-(morpholin-4-yl)-3-(naphthalen-2-yloxy)propan-2-ol compound, the method comprising: treating 2-((2naphthyloxy)methyl)oxirane with morpholine in a presence of triethylamine as a catalyst to obtain a crude product; purifying the crude product by recrystallization from absolute ethyl alcohol; and obtaining the 1-(morpholin-4-yl)-3-(naphthalen-2-yloxy)propan-2-ol compound.

These and other features of the present subject matter will become readily apparent upon further review of the following specification.

BRIEF DESCRIPTION OF THE DRAWINGS

The FIGURE shows an IR analysis of the 1-(morpholin-4-yl)-3-(naphthalen-2-yloxy)propan-2-ol compound.

DETAILED DESCRIPTION OF THE PREFERRED EMBODIMENTS

Figure 1:
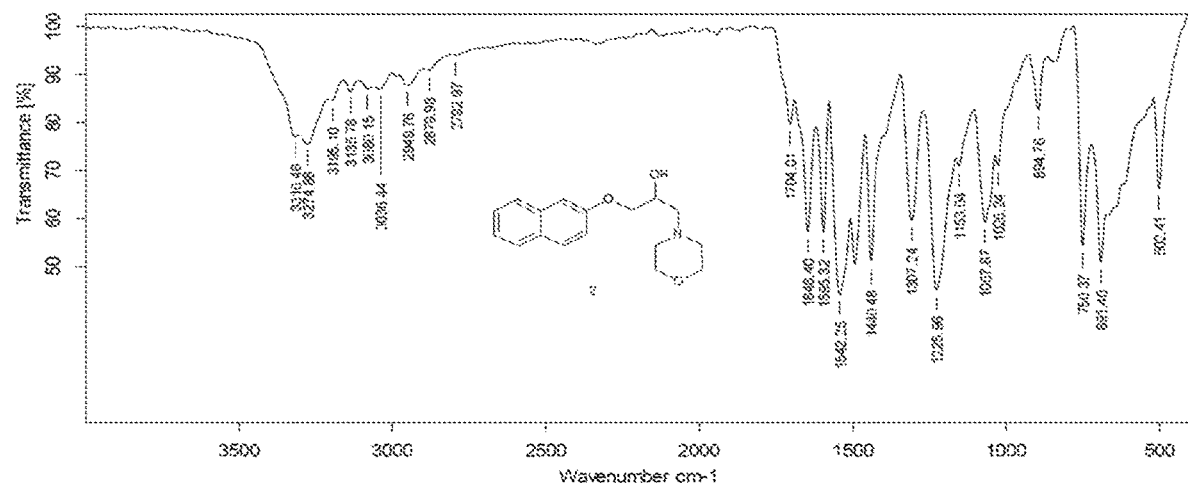
Figure 2:
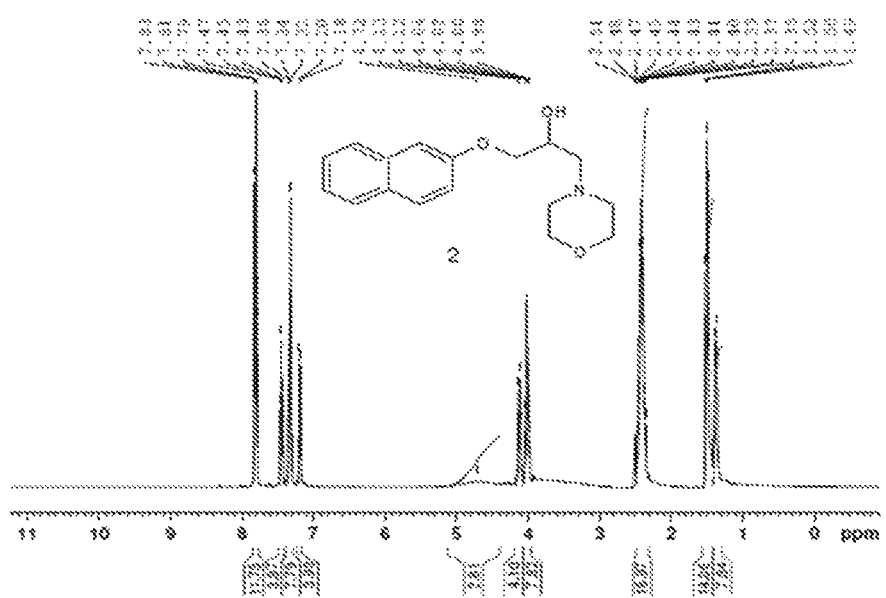
Figure 3:
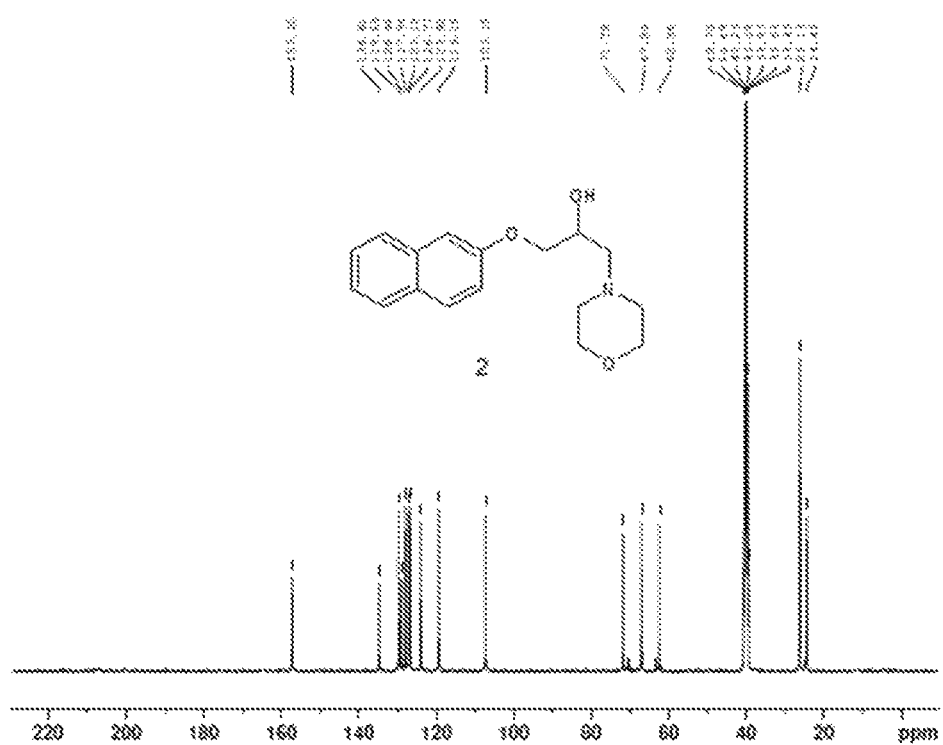

The following definitions are provided for the purpose of understanding the present subject matter and for construing the appended patent claims.

Definitions

Throughout the application, where compositions are described as having, including, or comprising specific components, or where processes are described as having, including, or comprising specific process steps, it is contemplated that compositions of the present teachings can also consist essentially of, or consist of, the recited components, and that the processes of the present teachings can also consist essentially of, or consist of, the recited process steps.

It is noted that, as used in this specification and the appended claims, the singular forms "a", "an", and "the" include plural references unless the context clearly dictates otherwise.

In the application, where an element or component is said to be included in and/or selected from a list of recited elements or components, it should be understood that the element or component can be any one of the recited elements or components, or the element or component can be selected from a group consisting of two or more of the recited elements or components. Further, it should be understood that elements and/or features of a composition or a method described herein can be combined in a variety of ways without departing from the spirit and scope of the present teachings, whether explicit or implicit herein.

The use of the terms "include," "includes", "including," "have," "has," or "having" should be generally understood as open-ended and non-limiting unless specifically stated otherwise.

The use of the singular herein includes the plural (and vice versa) unless specifically stated otherwise. In addition, where the use of the term "about" is before a quantitative value, the present teachings also include the specific quantitative value itself, unless specifically stated otherwise. As used herein, the term "about" refers to a ±10% variation from the nominal value unless otherwise indicated or inferred.

The term "optional" or "optionally" means that the subsequently described event or circumstance may or may not occur, and that the description includes instances where said event or circumstance occurs and instances in which it does not.

It will be understood by those skilled in the art with respect to any chemical group containing one or more substituents that such groups are not intended to introduce any substitution or substitution patterns that are sterically impractical and/or physically non-feasible.

Unless defined otherwise, all technical and scientific terms used herein have the same meaning as commonly understood to one of ordinary skill in the art to which the presently described subject matter pertains.

Where a range of values is provided, for example, concentration ranges, percentage ranges, or ratio ranges, it is understood that each intervening value, to the tenth of the unit of the lower limit, unless the context clearly dictates otherwise, between the upper and lower limit of that range and any other stated or intervening value in that stated range, is encompassed within the described subject matter. The upper and lower limits of these smaller ranges may independently be included in the smaller ranges, and such embodiments are also encompassed within the described subject matter, subject to any specifically excluded limit in the stated range. Where the stated range includes one or both of the limits, ranges excluding either or both of those included limits are also included in the described subject matter.

Throughout the application, descriptions of various embodiments use "comprising" language. However, it will be understood by one of skill in the art, that in some specific instances, an embodiment can alternatively be described using the language "consisting essentially of" or "consisting of".

For purposes of better understanding the present teachings and in no way limiting the scope of the teachings, unless otherwise indicated, all numbers expressing quantities, percentages or proportions, and other numerical values used in the specification and claims, are to be understood as being modified in all instances by the term "about". Accordingly, unless indicated to the contrary, the numerical parameters set forth in the following specification and attached claims are approximations that may vary depending upon the desired properties sought to be obtained. At the very least, each numerical parameter should at least be construed in light of the number of reported significant digits and by applying ordinary rounding techniques.

The present subject matter relates to the synthesis of a unique pure insect growth regulator, as well as the regulator itself. The structure of this synthesized compound, which is related to the most well-known insect growth regulator insecticides, can be confirmed by elemental and contemporary spectroscopic investigations (IR, UV, $^1$HNMR, $^{13}$CNMR, and elemental analysis). The insecticidal efficacy of the chemically newly synthesized compound was checked against *Spodoptera littoralis* under laboratory conditions and compared with fenoxycarb as a reference insecticide. It has been found that the present compound has a $LC_{50}=17.56$ mg/l, whereas fenoxycarb has a $LC_{50}=2.73$ mg/l, indicating the insecticidal effectiveness of the present compound.

In an embodiment, the present subject matter relates to a 1-(morpholin-4-yl)-3-(naphthalen-2-yloxy)propan-2-ol compound having the formula I:

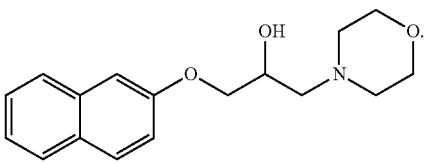

In certain embodiments, the 1-(morpholin-4-yl)-3-(naphthalen-2-yloxy)propan-2-ol compound can be obtained as a white powder. In further embodiments, the 1-(morpholin-4-yl)-3-(naphthalen-2-yloxy)propan-2-ol compound can have a melting point of about 112° C. to about 114° C.

In additional embodiments, the 1-(morpholin-4-yl)-3-(naphthalen-2-yloxy)propan-2-ol compound is considered as an insect growth regulator (IGR). Accordingly, the present compound is capable of inhibiting the life cycle of an insect.

In another embodiment, the present subject matter relates to an insecticidally acceptable composition comprising an insecticidally effective amount of the 1-(morpholin-4-yl)-3-(naphthalen-2-yloxy)propan-2-ol compound and an insecticidally acceptable carrier.

In some embodiments, the present compositions and methods of use can be used for combination treatment, where other insecticidal ingredients can be included therein, or can be co-administered therewith.

Non-limiting examples of suitable excipients, carriers, or vehicles useful herein include liquids such as water, saline, glycerol, polyethylene glycol, hyaluronic acid, ethanol, and the like. Suitable excipients for nonliquid formulations are also known to those of skill in the art.

The present compounds are typically administered at an insecticidally effective dosage, e.g., a dosage sufficient to provide a desired activity against insects.

While insecticidal dosage levels have yet to be optimized for the present compounds, generally, each treatment of the present compositions could be expected to include from about 12.5 ppm to about 200 ppm, or mg/L, of the present compounds. In this regard, compositions having concentrations of the present compounds of about 200 ppm, about 100 ppm, about 50 ppm, about 25 ppm, or about 12.5 ppm, or mg/L, per application to a desired area of treatment are included within the present subject matter. The precise effective amount will vary from treatment to treatment and will depend upon the target area of application, the insect species being treated for, the number of insects present, and the like. The treatment area may be administered as many doses as is required to produce an effective treatment.

Liquid compositions can, for example, be prepared by dissolving, dispersing, etc. the active compound as defined above and optional adjuvants in a carrier, such as, for example, water, saline, aqueous dextrose, glycerol, glycols, ethanol, and the like, to thereby form a solution or suspension. If desired, the composition to be administered may also contain minor amounts of nontoxic auxiliary substances such as wetting agents, emulsifying agents, or solubilizing agents, pH buffering agents and the like, for example, sodium acetate, sodium citrate, cyclodextrin derivatives, sorbitan monolaurate, triethanolamine acetate, triethanolamine oleate, etc.

In a further embodiment, the present subject matter relates to a method of killing insects comprising applying to said insects or to a target site of insect infestation an insecticidally effective amount of the 1-(morpholin-4-yl)-3-(naphthalen-2-yloxy)propan-2-ol compound or a composition containing the same.

In an embodiment, the present methods of killing insects can be effective against insects belonging to a species *Spodoptera littoralis* (Boisd.). Further, the present compound can be considered as an insect growth regulator (IGR) that inhibits the life cycle of an insect, particularly *Spodoptera littoralis*. Accordingly, the present compound can be used as an insecticide to control populations of harmful insect pests, including, by way of non-limiting example, cockroaches and fleas.

Unlike classic insecticides, the present compound is unlikely to affect an insect's nervous system and is thus more friendly to "worker insects" within closed environments. The present compound can also be more compatible with pest management systems that use biological controls. In addition, while insects can become resistant to insecticides, they are less likely to become resistant to the present compound.

In another embodiment, in the present methods of killing insects, the 1-(morpholin-4-yl)-3-(naphthalen-2-yloxy)propan-2-ol compound can have an $LC_{50}$ of about 17.56 ppm against the species *Spodoptera littoralis* after 72 hours of treatment. In this regard, in the present methods of killing insects, the 1-(morpholin-4-yl)-3-(naphthalen-2-yloxy)propan-2-ol compound can have an $LC_{50}$ of about 17.56 ppm against $2^{nd}$ instars of larvae of the species *Spodoptera littoralis* after 72 hours of treatment.

Similarly, in the present methods of killing insects, the 1-(morpholin-4-yl)-3-(naphthalen-2-yloxy)propan-2-ol compound can have an $LC_{50}$ of about 69.252 ppm against the species *Spodoptera littoralis* after 72 hours of treatment. In this regard, in the present methods of killing insects, the 1-(morpholin-4-yl)-3-(naphthalen-2-yloxy)propan-2-ol compound can have an $LC_{50}$ of about 69.252 ppm against $4^{th}$ instars of larvae of the species *Spodoptera littoralis* after 72 hours of treatment.

In a further embodiment of the present methods, the 1-(morpholin-4-yl)-3-(naphthalen-2-yloxy)propan-2-ol compound can be applied to castor leaves.

In an additional embodiment of the present methods, about 12.5 to about 200 ppm of the 1-(morpholin-4-yl)-3-(naphthalen-2-yloxy)propan-2-ol compound can be applied to the insects or to the target site. In this regard, about 200 ppm, about 100 ppm, about 50 ppm, about 25 ppm, or about 12.5 ppm, or mg/L, per application of the 1-(morpholin-4-yl)-3-(naphthalen-2-yloxy)propan-2-ol compound can be applied to a desired area of treatment.

In an additional embodiment, the present subject matter relates to a method of repelling insects comprising applying to a target site of insect infestation an insect repelling effective amount of the 1-(morpholin-4-yl)-3-(naphthalen-2-yloxy)propan-2-ol compound or a composition containing the same.

In an embodiment, the present methods of repelling insects can be effective against insects belonging to a species *Spodoptera littoralis* or *Spodoptera littoralis* (Boisd.).

In one more embodiment, the present subject matter relates to a method of controlling an insect pest comprising applying to a target site of insect infestation an insect controlling effective amount of the 1-(morpholin-4-yl)-3-(naphthalen-2-yloxy)propan-2-ol compound or a composition containing the same.

In an embodiment, the present methods of controlling insect pests can be effective against insects belonging to a species *Spodoptera littoralis* or *Spodoptera littoralis* (Boisd.).

In a further embodiment, the present subject matter relates to a method of making the 1-(morpholin-4-yl)-3-(naphthalen-2-yloxy)propan-2-ol compound, the method comprising: treating 2-((2naphthyloxy)methyl)oxirane with morpholine in a presence of triethylamine as a catalyst to obtain a crude product; purifying the crude product by recrystallization from absolute ethyl alcohol; and obtaining the 1-(morpholin-4-yl)-3-(naphthalen-2-yloxy)propan-2-ol compound.

The present production methods can be further seen by referring to the following Scheme 1:

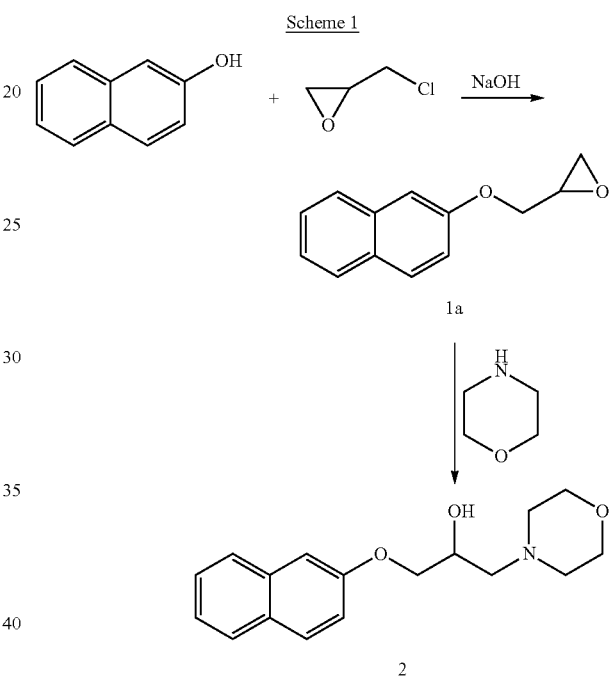

In an embodiment of the present production methods, the 1-(morpholin-4-yl)-3-(naphthalen-2-yloxy)propan-2-ol compound can be obtained as a white powder.

In another embodiment of the present production methods, the 1-(morpholin-4-yl)-3-(naphthalen-2-yloxy)propan-2-ol compound can be obtained in an about 60% yield.

The following examples relate to various methods of manufacturing certain specific compounds and application results as described herein. All compound numbers expressed herein are with reference to the synthetic pathway figures shown above.

EXAMPLES

Example 1

Preparation of 2-((2-naphthyloxy)methyl)oxirane

The target product, 2-((2-naphthyloxy)methyl)oxirane 1a was synthesized via the reaction of epichorohydrin with 2-naphthol in the presence of a suitable amount NaOH.

Example 2

Preparation of 1-(morpholin-4-yl)-3-(naphthalen-2-yloxy)propan-2-ol

The target product, 1-(morpholin-4-yl)-3-(naphthalen-2-yloxy)propan-2-ol 2 was synthesized via treatment of the appropriate 2-((2naphthyloxy)methyl)oxiran 1a with morpholine in the existence of triethylamine as a catalyst to obtain a crude product, which is then purified through recrystallization from the absolute ethyl alcohol to obtain the 1-(morpholin-4-yl)-3-(naphthalen-2-yloxy)propan-2-ol 2.

Characterization of the prepared compound using IR is shown in the sole figure. $^1$H NMR, and $^{13}$C NMR analysis was also conducted. The elemental analysis can be seen as follows.

1-(morpholin-4-yl)-3-(naphthalen-2-yloxy)propan-2-ol (2)

White powder, 60% yield, melting point: 112-114° C. (KBr) IR: (OH) at 3315, (NH) at 3273, (C—H aromatic) at 3081 (C—H aliphatic) at 2878 cm$^{-1}$. $^1$HNMR (DMSO-d$_6$): (m, 7H Ar—H) at δ 7.19-7.88, (s, 1H, OH) at 4.71, (s, 1H, CH) at 4.12, (s, 4H, 2CH$_2$) at 4.01, (m. 8H, 4CH$_2$) at 1.52. $^{13}$C NMR (DMSO-d$_6$): δ 157.21, 134.82, 129.68, 127.93, 127.20, 126.02, 125.76, 107.24, 71.78, 67.01, 62.33, 26.18, 24.63. Analysis Calculated/found C$_{17}$H$_{21}$NO$_3$: C, 71.06/71.05; H, 7.37/7.36; N, 4.87/4.86.

Example 3

Insecticidal Bioassay Screening

Five concentrations (200, 100, 50, 25, 12.5 ppm) were designed for this synthetic compound and the reference fenoxycarb compound as the dynamic ingredients based on ppm via diluting the commercial formulation.

In this experiment, castor leaves are immersed in each of the previously prepared concentrations of the components for 10 seconds and then left to dry for 60 minutes. Larvae of the second and fourth instars of each checked strain are prepared with treated leaves in gauze-covered glass containers for 72 hrs. An untreated control is made in which leaves are dipped in triton x-100 and distilled water only. Then the preserved leaves were removed & fresh, untreated leaves were provided for 72 hours. Three replicates (10 larvae each) were checked for each concentration. Daily inspection was carried out for all treatments and mortality percentages were recorded 3 days (72 hours) after treatment. The average mortality percentage was corrected employing Abbott's formula. The corrected mortality rate for each of the previously synthesized compounds is statistically calculated according to Finney (1970). Through this rate, the corresponding concentration test lines (LDP lines) are assessed. Fifty and ninety percent mortality are determined, and the regression values for the checked products were previously evaluated.

The results of the bioassay screening can be observed in Table 1, below.

TABLE 1

Insecticidal activity of 1-(morpholin-4-yl)-3-(naphthalen-2-yloxy)propan-2-ol and Fenoxycarb against the 2$^{nd}$ and 4$^{th}$ larvae of S. littoralis after 72 h of treatment.

| Compound | LC$_{50}$ (ppm) | slope ± SE | Toxic ratio[a] | LC$_{50}$ (ppm) | slope ± SE | Toxic ratio[a] |
|---|---|---|---|---|---|---|
| Fenoxycarb | 2.73 | 0.238 ± 0.082 | 100 | 43.231 | 0.251 ± 0.082 | 1 |
| 2 | 17.56 | 0.238 ± 0.076 | 15.5 | 69.252 | 0.255 ± 0.0862 | 62.4 |

Notes:
[a]Toxicity ratio is estimated as fenoxycarb's LC$_{50}$ value for baseline toxicity/the compounds' LC$_{50}$ value × 100.

From this data, it is observed that the present compound is active against *Spodoptera littoralis* as it is close in activity to the reference insecticide, fenoxycarb.

It is to be understood that the 1-(morpholin-4-yl)-3-(naphthalen-2-yloxy)propan-2-ol compound, compositions containing the same, and methods of using and producing the same are not limited to the specific embodiments described above, but encompasses any and all embodiments within the scope of the generic language of the following claims enabled by the embodiments described herein, or otherwise shown in the drawings or described above in terms sufficient to enable one of ordinary skill in the art to make and use the claimed subject matter.

We claim:

1. An insecticidally acceptable composition composing an insecticidally effective amount of a 1-(morpholin-4-yl)-3-(naphthalen-2-yloxy)propan-2-ol compound and an insecticidally acceptable carrier, wherein the 1-(morpholin-4-yl)-3-(naphthalen-2-yloxy)propan-2-ol compound has the formula I:

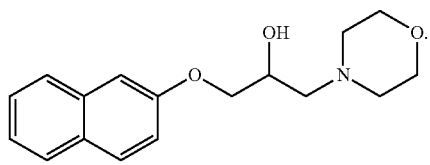

2. The insecticidally active composition of claim 1, wherein the compound is obtained as a white powder.

3. The insecticidally active composition of claim 1, having a melting point of about 112° C. to about 114° C.

4. A method of killing insects comprising applying to said insects or to a target site of insect infestation an insecticidally effective amount of the insecticidally active composition of claim 1.

5. The method of killing insects of claim 4, wherein the insects belong to a species *Spodoptera littoralis*.

6. The method of killing insects of claim 5, wherein the 1-(morpholin-4-yl)-3-(naphthalen-2-yloxy)propan-2-ol compound has an LC$_{50}$ of about 17.56 ppm against the species *Spodoptera littoralis* after 72 hours of treatment.

7. The method of killing insects of claim 5, wherein the 1-(morpholin-4-yl)-3-(naphthalen-2-yloxy)propan-2-ol compound has an LC$_{50}$ of about 17.56 ppm against 2$^{nd}$ instars of larvae of the species *Spodoptera littoralis* after 72 hours of treatment.

8. The method of killing insects of claim 5, wherein the 1-(morpholin-4-yl)-3-(naphthalen-2-yloxy)propan-2-ol compound has an LC$_{50}$ of about 69.252 ppm against the species *Spodoptera littoralis* after 72 hours of treatment.

9. The method of killing insects of claim 5, wherein the 1-(morpholin-4-yl)-3-(naphthalen-2-yloxy)propan-2-ol compound has an LC$_{50}$ of about 69.252 ppm against 4$^{th}$ instars of larvae of the species *Spodoptera littoralis* after 72 hours of treatment.

10. The method of killing insects of claim 4, wherein the 1-(morpholin-4-yl)-3-(naphthalen-2-yloxy)propan-2-ol compound is applied to castor leaves.

11. The method of killing insects of claim 5, wherein about 12.5 to about 200 ppm of the 1-(morpholin-4-yl)-3-(naphthalen-2-yloxy)propan-2-ol compound is applied to the insects or to the target site.

12. A method of repelling insects comprising applying to a target site of insect infestation an insect repelling effective amount of the insecticidally active composition of claim 1.

13. The method of repelling insects of claim 12, wherein the insects belong to a species *Spodoptera littoralis*.

14. A method of controlling an insect pest comprising applying to a target site of insect infestation an insect controlling effective amount of the insecticidally active composition of claim 1.

15. The method of controlling the insect pest of claim 14, wherein the insect pest belongs to a species *Spodoptera littoralis*.

16. A method of making the 1-(morpholin-4-yl)-3-(naphthalen-2-yloxy)propan-2-ol compound of claim 1, the method comprising;
    treating 2-((2naphthyloxy)methyl)oxirane with morpholine in a presence of triethylamine as a catalyst to obtain a crude product;
    purifying the crude product by recrystallization from absolute ethyl alcohol; and
    obtaining the 1-(morpholin-4-yl)-3-(naphthalen-2-yloxy) propan-2-ol compound.

17. The method of making the 1-(morpholin-4-yl)-3-(naphthalen-2-yloxy)propan-2-ol of claim 16, wherein the 1-(morpholin-4-yl)-3-(naphthalen-2-yloxy)propan-2-ol compound is obtained as a white powder.

18. The method of making the 1-(morpholin-4-yl)-3-(naphthalen-2-yloxy)propan-2-ol compound of claim 16, wherein the 1-(morpholin-4-yl)-3-(naphthalen-2-yloxy)propan-2-ol compound is obtained in an about 60% yield.

\* \* \* \* \*